United States Patent [19]

Makarova et al.

[11] Patent Number: 4,845,109

[45] Date of Patent: Jul. 4, 1989

[54] ALKOXY-AND PHENOXY ALKYL ESTERS OF 2,6-DIMETHYL-4-(2-DIFLUOROMETHOXY-PHENYL)-1,4-DIHYDROPYRIDINE-3,5-CARBOXYLIC ACID

[76] Inventors: Natalya V. Makarova, ulitsa Madones, 27, kv. 70; Egils A. Biseniex, ulitsa Talavas Gatve, II, kv. I5, both of Riga; Yan R. Uldrikis, ulitsa Darza, 2, kv. 2, Elgava; Gunar Y. Dubur, ulitsa Ierikju, 43, kv. 2, Riga; Maris M. Veveris, ulitsa Veyavas, IO/2, kv. 20, Riga; Agris A. Kimenis, ulitsa Staitseles, I5, kv. 208, Riga, all of U.S.S.R.

[21] Appl. No.: 219,843

[22] Filed: Jul. 8, 1988

Related U.S. Application Data

[63] Continuation of Ser. No. 49,010, May 11, 1987, abandoned, which is a continuation of Ser. No. 777,367, Sep. 18, 1985, abandoned.

[51] Int. Cl.$^4$ .................. C07D 211/86; A61K 31/455
[52] U.S. Cl. ...................................... 514/356; 546/321
[58] Field of Search .......................... 546/321; 514/356

[56] References Cited

U.S. PATENT DOCUMENTS 4,492,703 . 1/1985 Goldmann et al. .................. 546/321

FOREIGN PATENT DOCUMENTS 2569286 12/1979 U.S.S.R. .

OTHER PUBLICATIONS

Remington's Pharmaceutical Sciences, 14th Edition (1970).

Primary Examiner—Jane T. Fan
Attorney, Agent, or Firm—Burgess, Ryan and Wayne

[57] ABSTRACT

Novel compounds, that is, alkoxy- and phenoxy-alkyl esters of 2,6-dimethyl-4-(2-difluoromethoxyphenyl)-1,4-dihydropyridine-3,5-dicarboxylic acid have the following general formula useful for producing hypotensive and vasodilation effects.

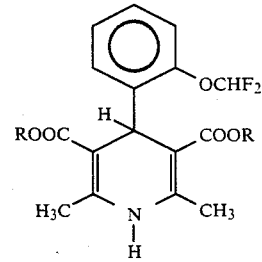

8 Claims, No Drawings

ALKOXY-AND PHENOXY ALKYL ESTERS OF 2,6-DIMETHYL-4-(2-DIFLUOROMETHOXY-PHENYL)-1,4-DIHYDROPYRIDINE-3,5-CARBOXYLIC ACID

This application is a continuation of application Ser. No. 049,010, filed 05/11/87 now abandoned, which is a continuation of Ser. No. 777,367, filed 09/18/85 now abandoned.

FIELD OF THE INVENTION

The present invention relates to organic chemistry and more specifically is concerned with novel compounds, viz, alkoxy- and phenoxy-alkyl esters of 2,6-dimethyl-4-(2-difluoromethoxyphenyl)-1,4-dihydropyridine-3,5-dicarboxylic acid, producing hypotensive and vasodilation effects, predominantly on cardiac and cerebral vessels, and therefore applicable in medicine.

BACKGROUND ART

It is common knowledge that 2,6-dimethyl-3,5-dimethoxycarbonyl-4-(2-nitrophenyl)-1,4-dihydropyrine (preparation Niphedipin) cf. W. Vater et al. Pharmacology of dimethyl ester of 4-(2'-nitrophenyl)-2,6dimethyl-1,4-dihydropyridine-3,5-dicarboxylic acid. Arzneimittel-Forschung, 1972, Bd. 22 (1), S.1/ and 2,6-dimethyl-3,5-dimethoxycarbonyl-4-(2-difluoromethoxyphenyl)-1,4-dihydropyridine (cf. USSR Inventor's Certificate No. 706,410, Cl. C 07 D 211/90, A 61 K 31/44, 1979). The medicinal preparations mentioned above are highly toxic. In addition, Niphedipin is occasionally causative of dizziness and nausea and is a light-instable drug.

Known in the art is also 2,6-dimethyl-3-methoxy-carbonyl-4-(3-nitrophenyl)-5-[2(N-benzyl-N-methylamino)ethoxycarbonyl]-1,4-dihydropyridine hydrochloride (preparation Nicardipin), possessing vasodilation activity preponderantly towards cerebral vessels (cf. Takenaka T. Usuda S., Nomura T., Maeno H., Sado T., Arzneimittel-Forschung, 1976, Bd. 26, No. 12, S. 2172–2178).

The aforesaid compound is featured by inadequate activity and a very complicated process for its production.

The compounds disclosed in the invention are novel and have not so far been described in literature.

The invention has for its object to provide novel compounds capable of producing high hypotensive and vasodilation effects being at the same time of low toxicity.

SUMMARY OF THE INVENTION

The object of the invention is accomplished due to the fact that, according to the invention, the herein-disclosed compounds, viz, alkoxy- and phenoxy-alkyl esters of 2,6-dimethyl-4-(2-difluoromethoxyphenyl)-1,4-dihydropyridine-3,5-dicarboxylic acid have the following general formula:

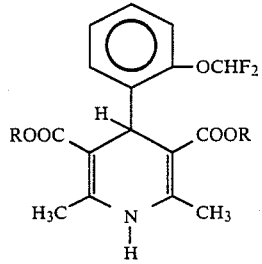

(I)

where R = $C_2H_4OCH_3$; $C_2H_4OC_2H_5$; $C_2H_4OC_3H_7$;
$C_2H_4OC_6H_5$;
$CH(CH_3)CH_2OCH_3$

DETAILED DESCRIPTION OF THE INVENTION

The compounds disclosed herein appear as light-yellow crystalline substances, insoluble in water and comparatively readily dissolvable in ethanol, chloroform, and many other organic solvents. The compounds are chemically stable.

Biological potency of the compounds under consideration has been studied in experiments on test animals.

There have been studied specific (vasodilation and hypotensive) action of the compounds in question and their acute toxicity. For comparison use has been of the known highly potent vasodilation and hypotensive drugs Niphedipin (Phenihydin), Nicardipin(Perdipin), and 2,6-dimethyl-3,5-dimethoxycarbonyl-4-(2-difluoromethoxyphenyl)-1,4-dihydropyridine.

The aforesaid compounds have been tested experimentally on cats, dogs, rats, and mice.

In acute experiments on cats narcotized with glucochloralose and urethane (90 and 200 mg/kg, respectively, administered intraperitoneally), there were recorded arterial pressure from the common carotid artery, respiration and an ECG with standard lead II. The compounds under study were administered intravenously as a dimethylacetamide solution. It has been found that all the compounds under study are capable of producing a pronounced reduction of arterial pressure, the numerical findings being tabulated in Table 1 below. The compounds being disclosed feature higher hypotensive activity compared with the heretofore-known ones. The most potent of the compounds of this invention, i.e., 2,6-dimethyl-3,5-bis-(2-propoxyethoxycarbonyl)-4-(2-difluoromethoxyphenyl)-1,4-dihydropyridine, causes a reduction of the arterial pressure, when administered to cats intravenously, at as low doses as 0.0005 to 0.001 mg/kg. It has been revealed that the compounds of the invention, unlike Niphedipin and 2,6-dimethyl-3,5-dimethoxycarbonyl-4-(2-difluoromethoxyphenyl)-1,4-dihydropyridine, reduce the diastolic arterial pressure more conspicuously than the systolic one. Hence when administered in the dose range tested (0.0005 to 0.1 mg/kg) the compounds of the invention are capable of reducing the peripheral resistance to a greater extent than the known compounds and inhibit the cardiac contraction force to a less extent.

A pronounced hypotensive activity of the compounds under consideration has been corroborated in experiments on rats narcotized with urethane (1200 mg/kg) administered intraperitoneally. In addition, it has been established that, when administered in doses close to $ED_{30}$, the compounds of the invention on allay much the spasmogenic effect of angiotensin by reducing a hypertensive reaction caused by the latter, by 20 to 30 percent.

In acute experiments on dogs having body mass of 11 to 19 kg and narcotized with ethaminal sodium (40 mg/kg) administered intraperitoneally, the compounds of the invention produce a considerable increase in the volumetric blood circulation rate in the arteries supplying blood to the heart and brain, while giving no substantial effect upon the systolic arterial pressure. Thus, the compound of the invention, i.e., 2,6-dimethyl-3,5-bis-(2-propoxyethoxycarbonyl)-4-difluoromethoxyphenyl)-1,4-dihydropyridine, administered intravenously in a dose of 0.001 mg/kg, increases the volumetric circulation rate in the vertebral, carotid and coronary arteries by 90, 60 and 30 percent respectively. Hence the compound in question is much more potent, as for the intensity and duration of the aforesaid effect, than Nicardipin, a renowned dilator of the cerebral vessels. The investigaion findings are represented in Table 2 below. The blood flow velocity in the femoral artery of the test dogs is found to increase considerably only in response to higher doses of the drug, which are also causative of a drop of the systemic arterial pressure.

In experiments on spontaneously hypertensive rats (SHR) given the compounds of the invention orally in a dose of 3 and 10 mg/kg, the systolic arterial pressure has been observed to fall for a period of six hours and more. The most markedly pronounced hypotensive potency is exhibited by the compounds of the invention, i.e. 2,6-dimethyl-3,5-bis-(2-ethoxyethoxycarbonyl)-4-(2-difluoromethoxyphenyl)-1,4-dihydropyridine, 2,6-dimethyl-3,5-bis-(2-propoxyethoxycarbonyl)-4-(2-difluoromethoxyphenyl)-1,4-dihydropyridine, and 2,6-dimethyl-3,5-bis-(2-phenoxyethoxycarbonyl)-4-(2-difluoromethoxyphenyl)-1,4-dihydropyridine. The hypotensive effect produced by the compounds mentioned above does not differ substantially from the given by Niphedipin but, unlike the latter, such a compound of the invention as 2,6-dimethyl-3,5-bis-(2-ethoxyethoxycarbonyl)-4-(2-difluoromethoxyphenyl)-1,4-dihydropyridine is not causative of tachycardia.

It has been established, when studying acute toxicity of the compounds involved on albino mice given the drug intragperitoneally, that the compounds of the invention is of low toxicity, the investigation results being tabulated in Table 3 below. The most potent compound has been found to exhibit acute toxicity 2.3 times as low as Niphedipin does, while the rest of the compounds are 5 to 13 times less toxic than Niphedipin.

TABLE 1

Average doses of the compounds under study that reduce the arterial pressure in narcotized animals by 30%

| | | Hypotensive potency | | |
|---|---|---|---|---|
| | | cats | | rats |
| Nos. | Compound | $ED_{30}$ mg/kg | Persistence, min | $ED_{30}$, mg/kg |
| | Compound of the invention of Formula 1, where | | | |
| 1 | R = $C_2H_4OCH_3$ | 0.045 | 3 | 0.04 |
| 2 | R = $C_2H_4OC_2H_5$ | 0.010 | 6 | 0.018 |
| 3 | R = $C_2H_4OC_3H_7$ | 0.0045 | 7 | 0.008 |
| 4 | R = $C_2H_4OC_6H_5$ | 0.020 | 7 | 0.03 |
| 5 | R = $CH(CH_3)CH_2OCH_3$ | 0.038 | 10 | — |
| 6 | Niphedipin | 0.020 | 6 | — |
| | 2,6-dimethyl-3,5-dimethoxycarbonyl- | 0.023 | 8 | 0.03 |

TABLE 1-continued

Average doses of the compounds under study that reduce the arterial pressure in narcotized animals by 30%

| | | Hypotensive potency | | |
|---|---|---|---|---|
| | | cats | | rats |
| Nos. | Compound | $ED_{30}$ mg/kg | Persistence, min | $ED_{30}$, mg/kg |
| | 4-(2-difluoromethoxyphenyl)-1,4-dihydropyridine | | | |
| 7 | Nicardipin | 0.025 | 8 | — |

TABLE 2

Effects produced by the compound of the invention (of Formula 1, where R = $C_2H_4OC_3H_7$) and by Nicardipin upon blood circulation rate in the vertebral, carotid and femoral arteries in experiments on narcotized dogs

| | | | Blood circulation rate in vertebral artery | |
|---|---|---|---|---|
| Nos 1 | Compound 2 | Dose, mg/kg 3 | percentage increase 4 | persistence, min 5 |
| 1. | Compound of the invention | 0.0005 | 20 | 8 |
| 2. | Same | 0.001 | 90 | 18 |
| 3. | Same | 0.002 | 110 | 20 |
| 4. | Nicardipin | 0.001 | 14 | 6 |
| 5. | Same | 0.002 | 40 | 20 |

| | Blood circulation rate in carotid artery | | Blood circulation rate in coronary artery | | Blood circulation rate in femoral artery | |
|---|---|---|---|---|---|---|
| Nos. 1 | percentage increase 6 | persistence min 7 | percentage increase 8 | persistence min 9 | percentage increase 10 | persistence min 11 |
| 1 | 17 | 5 | 10 | 5 | 0 | — |
| 2 | 60 | 15 | 30 | 8 | 10 | 8 |
| 3 | 100 | 20 | 50 | 12 | 25 | 10 |
| 4 | 14 | 6 | 12 | 5 | 10 | 5 |
| 5 | 60 | 12 | 30 | 12 | 26 | 10 |

TABLE 3

Acute toxicity of the compounds involved compared with the known drugs tested on albino mice (intraperitoneal administration)

| Compound | $LD_{50}$, mg/kg |
|---|---|
| Compound of the invention of Formula 1, where | |
| R = $C_2H_4OCH_3$ | 1130 (869.2 to 1469) |
| R = $C_2H_4OC_2H_5$ | 2200 (1654 tp 2926) |
| R = $C_2H_4OC_3H_7$ | 450 (357 to 567) |
| R = $C_2H_4OC_5H_5$ | 790 (556.3 to 1121.8) |
| R = $CH(CH_3)CH_2OCH_3$ | 2500 (1724 to 3625) |
| Niphedipin | 190 (146.15 to 247) |
| 2,6-dimethyl-3,5-dimethoxycarbonyl-4-(2-difluoromethoxyphenyl)-1,4-dihydropyridine | 395 (250 to 460) |
| Nicardipin | 225 (169.1 to 299.25) |

On the grounds of the data obtained one may recognize a number of advantages of the compound being disclosed over the known drugs of the same character:

high and selective vasodilation potency towards the vessels supply blood to the brain and heart;

high hypotensive activity both upon intravenous and peroral administration;

unlike Niphedipin the compounds of the invention cause no perceptible tachycardia in nonnarcotized animals;

low toxicity (2.3 to 13 times as low as that of Niphedipin), which is decisive in a wide range of therapeutic effects.

The compounds of the invention can be produced using a known technique by virtue of interreaction of acetoacetates of a general formula

CH$_3$COCH$_2$COOR, where R=C$_2$H$_4$OCH$_3$, C$_2$H$_4$OC$_2$H$_5$, C$_2$H$_4$OC$_3$H$_7$, C$_2$H$_4$OC$_6$H$_5$, CH(CH$_3$)CH$_2$OCH$_3$ with 2-difluoromethoxybenzaldehyde and ammonia upon heating in an organic solvent, preferably ethanol.

The process proceeds according to the following reaction pattern:

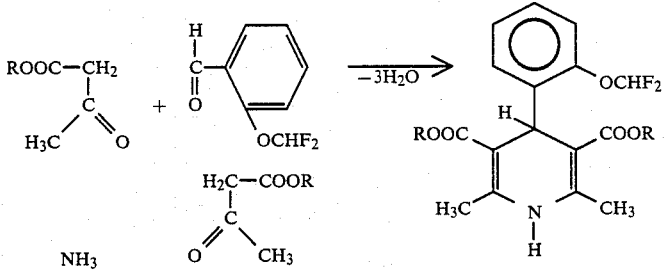

where R = C$_2$H$_4$OCH$_3$, C$_2$H$_4$OC$_2$H$_5$, C$_2$H$_4$OC$_3$H$_7$, C$_2$H$_4$OC$_6$H$_5$, CH(CH$_3$)CH$_2$OCH$_3$ To promote understanding of the present invention given below are the following examples of production of the compounds being disclosed.

EXAMPLE 1

24.0 g (0.15 mole) methoxyethyl acetoacetate and 12.9 g (0.075 mole) 25-percent aqueous ammonia are dissolved in 50 ml ethanol and boiled for six hours. Upon cooling the reaction mixture is allowed to stand for 24 hours, whereupon the fallen-out precipitate is filtered and dried at room temperature to obtain 21.2 g (68%) 2,6-dimethyl-3,5-bis-(2-methoxyethoxycarbonyl)-4-(2-difluoromethoxyphenyl)-1,4-dihydropyridine, which appears as a light-yellow crystalline substance. M.p. 94° to 95° C. (from ethanol).

Found, %: C 58.2; H 6.3; N 2.8 C$_{22}$H$_{27}$NO$_7$F$_2$. Calculated, %: C 58.0; H 6.0; N 3.1.

Paramagnetic resonance spectrum in CDCl$_3$, E: 2.24 (s., 6H, 2,6—CH$_3$); 3.25 (s., 6H, 3,5—CH$_3$); 3.51 (t., 4H, 3,5—CH$_2$—O, I=5 Hz); 4.12 (t., 4H 3,5—COOCH$_2$—, J=5 Hz); 5.27 (c., 1H, 4-H); 5.89 (b.s., 1H, N—H); 6.55 (t., 1H, —OCHF$_2$, J=75 Hz); 6.92-7.42 p.p.m. (m., 4H, —C$_6$H$_4$—).

UV spectrum in ethanol, λ$_{max}$ (Log): 206 (4.18), 239 (4.28) and 362 nm (3.85).

IR spectrum in vaseline oil: 1700 cm$^{-1}$ (C=O), 3180 cm$^{-1}$ (NH).

EXAMPLE 2

There are taken 34.8 g (0.2 mole) ethoxyethyl acetoacetate, 17.2 g (0.1 mole) 2-difluoromethoxybenzaldehyde and 10 ml (0.13 mole) 25-percent aqueous ammonia to obtain, in a way similar to that described in Example 1, 30.2 g (62.5%) 2,6-dimethyl-3,5-bis-(2-ethoxyethoxycarbonyl)-4-(2-difluoromethoxyphenyl)-1,4-dihydropyridine, appearing as a light-yellow crystalline substance. M.P. 123° to 124° C. (from ethanol).

Found, %: C 59.3; H 6.3; N 2.6; C$_{24}$H$_{31}$NO$_7$F$_2$. Calculated, %: C 59.6; H 6.5; N 2.9.

PMR spectrum in CDCl$_3$, δ 1.17 (t., 6H, 3,5—CH$_3$, J=7 Hz); 2.29 (s., 6H, 2,6—CH$_3$); 3.45 (q., 4H, 3,5—OCH$_2$—, J=7 Hz); 3.55 (t., 4H, 3,5—β—CH$_2$, J=5 Hz); 4.14 (t., 4H, 3,5—COOCH$_2$—, J=5 Hz); 5.26 (s., 1H, 4-H); 5.84 (b.s., 1H, N—H); 6.56 (t., 1H, —OCHF$_2$, J=75 Hz) 6.9-7.42 m.d. (m., 4H —C$_6$H$_4$—).

UF spectrum in ethanol, λ$_{max}$ (1 gє): 207 (4.23), 239 (4.33) and 362 nm (3.89)

IR spectrum in vaseline oil: 1697 cm$^{-1}$; 3330 cm$^{-1}$(NH).

EXAMPLE 3

There are taken 37.6 g (0.2 mole) propoxyethyl acetoacetate, 17.2 g (0.1 mole) 2-difluoromethoxybenzaldehyde and 10 ml (0.13 mole) 25-percent aqueous ammonia to obtain, using the process of Example 1, 27.4 g (55%) 2,6-dimethyl-3,5-bis-(2-propoxyethoxycarbonyl)-4-(2-difluoromethoxyphenyl)-1,4-dihydropyridine, appearing as a light-yellow crystalline substance. M.P. 97° to 98° C. (from ethanol).

Found %: C 60.4; H 7.4; N 2.5. C$_{26}$H$_{35}$NO$_7$F$_2$ Calculated, %: C 60; H 7.1; N 2.8.

PMR spectrum in CDCl$_3$, δ: 0.89 (t., 6H, 3.5—CH$_3$, J=7 Hz); 1.35-1.75 (m., 4H, 3,5—β—CH$_2$, J=7 Hz); 2.28 (s., 6H, 2,6—CH$_3$); 3.34 (t., 4H, 3,5—α—CH$_2$, J=7 Hz); 3.55 (t., 4H, 3,5—OCH$_2$OC—, J=5 Hz); 4.14 (t., 4H, 3,5—COOCH$_2$—, J=5 Hz); 5.25 (s., 1H 4-H); 5.82 (b.s., 1H, N—H); 6.55 (t., 1H, —OCHF$_2$, J=75 Hz); 6.9-7.42 p.p.m.(m., 4H, —C$_6$H$_4$—).

UV spectrum in ethanol, λ$_{max}$ (1 gє): 206 (4.19), 238 (4.30) and 362 nm (3.86).

IR spectrum in vaseline oil: 1697 cm$^{-1}$ (C=O); 3320 cm$^{-1}$ (NH).

EXAMPLE 4

There are taken 22.2 g (0.1 mole) phenoxyethyl acetoacetate, 8.6 g (0.05 mole) 2-difluoromethoxybenzaldehyde and 6.6 ml (0.09 mole) 25-percent aqueous ammonia to obtain, using the process of Example 1, 16.5 g (57%) 2,6-dimethyl-3,5-bis-(2phenoxyethoxycarbonyl)-4-(2difluoromethoxyphenyl)-1,4-dihydropyridine appearing as a light-yellow crystalline substance. M.p. 67° to 69° C. (from ethanol).

Found, %: C 66.6; H 5.7; N 2.4. C$_{32}$H$_{31}$NF$_2$O$_7$. Calculated, %: C 66.3; H 5.4; N 2.4.

PMR spectrum in CDCl$_3$, δ: 2.28 (c., 6H, 2,6—CH$_3$); 4.06 (t., 4H, 3,5—CCH$_2$O—, J=5 Hz); 4.34 (t., 4H, 3,5—COOCH$_2$—, J=5 Hz); 5.25 (s., 1H, 4-H); 5.75 (b.s., 1H, N—H); 6.48 (t., 1H, —OCHF$_2$, J=75 Hz); 6.76-7.37 p.p.m. (m. 14H, 4—C$_6$H$_4$— and 3,5—C$_6$H$_5$).

UV spectrum in ethanol, $\lambda_{max}$ (1 gε): 210 (4.38), 222 (4.38), 239 (4.28), 270 (3.68), 277 (3.56) and 364 nm (3.83).

IR spectrum in vaseline oil: 1702 cm$^{-1}$ (C=O); 3300 cm$^{-1}$ (NH).

EXAMPLE 5

There are taken 34.8 g (0.2 mole) 1-methoxy-2-propyl acetoacetate, 17.2 (0.1 mole) 2-difluoromethoxybenzaldehyde and 10 ml (0.13 mole) 25-percent aqueous ammonia to obtain, in a way similar to that of Example 1, 20.3 g (42%) 2,6-dimethyl-3,5-bis-[(1-methyl-2-methoxy)-ethoxycarbonyl]-4-(2-difluoromethoxyphenyl)-1,4-dihydropyridine appearing as a colourless crystalline substance. M.p. 147° to 148° C. (from ethanol).

Found, %: C 59.3; H 6.5; N 2.6. $C_{24}H_{31}NO_7F_2$. Calculated, %: C 59.6; H 6.5; N 2.9.

PMR spectrum in CDCl$_3$, δ: 1.04 (d., 3H, 3—COOCHCH$_3$—, J=7 Hz); 1.2 (d., 3H, 5—COOCCH$_3$—, J=7 Hz); 2.25 (c., 6H, 2,6—CH$_3$); 3.19 (s., 3H, 3—OCH$_3$); 3,2–3,58 (m., 4H, 3,5—CH$_2$); 3.33 (s., 3H, 5—OCH$_3$); 4.83–5.15 (m. 2H, 3,5—COOCH—); 5.22 (s., 1H, 4-H); 5.78 (b.s., 1H, N—H); 6.52 (t., 1H, —OCHF$_2$, J=75 Hz); 6.9–7.4 p.p.m. (m., 4H, —C$_6$H$_4$—).

UV spectrum in ethanol, $\lambda_{max}$ (1 gε): 207 (4.22), 239 (4.30), 363 nm (3.86).

IR spectrum in vaseline oil: 1700 cm$^{-1}$ (C=O); 3280 cm$^{-1}$ (NH).

The compound of the invention features high hypotensive potency and produces no perceptible tachycardia; it also produces high selective vasodilation effects upon the vessels supplying blood to the brain and heart.

What we claim is:

1. A compound selected from the group consisting of:
    2,6-dimethyl-3,5-bis-(2-ethoxyethoxycarbonyl)-4-(2-difluoromethoxyphenyl)-1,4-dihydropyridine,
    2,6-dimethyl-3,5-bis-(2-propoxyethoxycarbonyl)-4-(2-difluoromethoxyphenyl)-1,4-dihydropyridine, and
    2,6-dimethyl-3,5-bis-(2-phenoxyethoxycarbonyl)-4-(2-difluoromethoxyphenyl)-1,4-dihydropyridine.

2. The compound of claim 1 which is 2,6-dimethyl-3,5bis-(2-ethoxyethoxycarbonyl)-4-(2-difluoromethoxyphenyl)-1,4-dihydropyridine.

3. The compound of claim 1 which is 2,6-dimethyl-3,5-bis-(2-propoxyethoxycarbonyl)-4-(2-difluoromethoxyphenyl)-1,4-dihydropyridine.

4. The compound of claim 1 which is 2,6-dimethyl-3,5-bis-(2-phenoxyethoxycarbonyl)-4-(2-difluoromethoxyphenyl)-1,4-dihydropyridine.

5. A method for treating a patient in need of a cerebral vasodilation which comprises administering to said patient a cerebral vasodilating-effective amount of a compound selected from the group consisting of:
    2,6-dimethyl-3,5-bis-(2-ethoxyethoxycarbonyl)-4-(2-difluoromethoxyphenyl)-1,4-dihydropyridine,
    2,6-dimethyl-3,5-bis-(2-propoxyethoxycarbonyl)-4-(2-difluoromethoxyphenyl)-1,4-dihydropyridine, and
    2,6-dimethyl-3,5-bis-(2-phenoxyethoxycarbonyl)-4-(2-difluoromethoxyphenyl)-1,4-dihydropyridine.

6. The method of claim 5 wherein the compound is 2,6-dimethyl-3,5-bis-(2ethoxyethoxycarbonyl)-4-(2-difluoromethoxyphenyl)-1,4-dihydropyridine.

7. The method of claim 5 wherein the compound is 2,6-dimethyl-3,5-bis-(2-propoxyethoxycarbonyl)-4-(2-difluoromethoxyphenyl)-1,4-dihydropyridine.

8. The method of claim 5 wherein the compound is 2,6-dimethyl-3,5-bis-(2-phenoxyethoxycarbonyl)-4-(2-difluoromethoxyphenyl)-1,4-dihydropyridine.

* * * * *